United States Patent [19]

Kern et al.

[11] Patent Number: 4,624,960
[45] Date of Patent: Nov. 25, 1986

[54] SEDATIVE HAVING ANALGESIC AND BRADYCARDIAC PROPERTIES

[75] Inventors: Otto Kern; Franz Wilhelm, both of Ingelheim am Rhein, Fed. Rep. of Germany

[73] Assignee: Boehringer Ingelheim Vetmedica GmbH, Ingelheim am Rhein, Fed. Rep. of Germany

[21] Appl. No.: 786,841

[22] Filed: Oct. 11, 1985

[30] Foreign Application Priority Data

Oct. 15, 1984 [DE] Fed. Rep. of Germany ....... 3437694

[51] Int. Cl.$^4$ ........................................... A61K 31/415
[52] U.S. Cl. .................................................. 514/401
[58] Field of Search ........................................ 514/401

[56] References Cited

U.S. PATENT DOCUMENTS 4,166,859  9/1979  Stähle et al. ........................ 548/337

*Primary Examiner*—Stanley J. Friedman
*Attorney, Agent, or Firm*—Hammond & Littell, Weissenberger & Dippert

[57] ABSTRACT

The invention relates to the use of a substance as a sedative with an analgesic and bradycardiac effect in warm-blooded animals. The possible applications are, for example, in the field of veterinary medicine for general tranquilizing and for producing analgesia.

6 Claims, No Drawings

SEDATIVE HAVING ANALGESIC AND BRADYCARDIAC PROPERTIES

The invention relates to a sedative. More particularly, the invention relates to a sedative having analgesic and bradycardiac activity and to the use thereof.

German Pat. No. 2,630,060, which corresponds to U.S. Pat. No. 4,166,859, discloses the synthesis of 2-[(2-bromo-6-fluorophenyl)-imino]-imidazolidine(I). This compound is described as having a hypotensive activity as its pharmacological property.

In the search for a substance which could be used as a sedative for pigs, the compound described in German Pat. No. 2,630,060 and the addition salts thereof were unexpectedly found to be particularly effective. The surprising fact was that the sedative effect was predominant, obviously specific to the species, and any possible lowering of blood pressure was observed only as a minor side effect but not, as might have been expected, as the main effect.

In further tests, the compound has also proven effective in other warm-blooded animals such as ruminants, horses, and poultry. These tests also demonstrated an analgesic effect in addition to the sedative property.

The compound may also be used to intensify and prolong the activity of other substances, e.g., hypnotics or narcotics.

A particularly advantageous feature is the fact that 2-[(2-bromo-6-fluorophenyl)-imino]-imidazolidine and the acid addition salts thereof have a marked bradycardiac effect. Thus, in addition to the general sedation, the heart is also directly relieved from states of excitation, which is not the case with the conventional neuroleptics of the phenothiazine or haloperidol series.

The compound, i.e., 2-[(2-bromo-6-fluorophenyl)-imino]-imidazolidine or an acid addition salt thereof, is superior when used as a sedative with an analgesic and bradycardiac effect, even compared with the compound which is most structurally similar, namely, the dichlorophenyl derivative. This superiority can be demonstrated by the comparison of the analgesic and bradycardiac effects set forth in the following table:

TABLE 1

| Compound | Writhing Test ($ED_{50}$) (mg/kg) | Bradycardiac Effect ($ED_{60}$) (mg/kg) |
|---|---|---|
| 2-[(2-Bromo-6-fluorophenyl)-imino]-imidazolidine (I).HCl | 0.004 | 0.003 |
| 2-[(2,6-Dichlorophenyl)-imino]-imidazolidine.HCl | 0.017 | 0.010 |

The advantageous interaction of the sedative, analgesic, and bradycardiac properties of the compound opens up a wide spectrum of possible uses for this substance in veterinary medicine. For example, the compound could be used for the treatment of stress conditions induced by, for example, overcrowding of sleeping and feeding areas, fights for supremacy, travel, or birth; to prevent mother sows from eating their young; in neuroleptanalgesia and anaesthesia; or for the sedation and immobilization of wild animals.

After reaction with an inorganic or organic acid, the compound (I) may be used in the form of its pharmacologically acceptable salts. Acids which have proved suitable for this include, for example, hydrochloric, hydrobromic, sulfuric, phosphoric, tartaric, fumaric, citric, maleic, succinic, gluconic, malic, p-toluenesulfonic, methanesulfonic, and amidosulfonic acid.

If the compound (I) or an acid addition salt thereof, or a mixture of two or more thereof, are to be used as active substances in the manner discussed above, the preparations used may also contain one or more pharmacologically active substances from other groups of pharmaceutical products. The active substances may be administered to warm-blooded animals or humans orally, parenterally, rectally, or dermally as active ingredients in customary preparation forms suitable for the intended purposes, that is, compositions consisting essentially of one or more inert conventional carriers and/or diluents, e.g., corn starch, lactose, glucose, microcrystalline cellulose, magnesium stearate, polyvinyl pyrrolidone, citric acid, tartaric acid, water, water/ethanol, water/glycerol, water/sorbitol, water/polyethylene, glycol, propylene glycol, carboxymethylcellulose, or fatty substances such as hard fat, or suitable mixtures thereof, and an effective amount of the active ingredient, such as tablets, coated tablets, capsules, powders, suppositories, syrups, solutions, suspensions, emulsions, infusions, ampules, and drops. Oral preparations, for example, solutions, powders, tablets, or capsules, may be administered directly or added to drinking water or food. Advantageously the active substance or a mixture of different active substances may be administerd to humans or animals in a dosage generally of from about 0.002 to 5.0 mg/kg of body weight, preferably from about 0.006 to 0.8 mg/kg of body weight. A particular advantage is that the active substance is effective in this dosage range not only after injection but also after oral administration.

Dependent upon the type and severity of the affliction, upon the type of preparation, upon the route of administration, as well as upon the period or interval over which the administration takes place, it may, however, be necessary to deviate from the above dosages. Thus, it may be sufficient in some cases to administer more or less than the above-mentioned amounts of active ingredient. The optimum dosage and route of administration of active ingredient necessary in each case can easily be determined by one skilled in the art. However, irrespective of the method of administration, the effect of the active substance can be increased in intensity and duration as a function.

For parenteral injection, a from about 0.1 to 1% aqueous solution of 2-[(2-bromo-6-fluorophenyl)-imino]-imidazolidine hydrochloride is preferred.

The following table sets forth the correlation between activity and dosage of 2-[(2-bromo-6-fluorophenyl)-imino]-imidazolidine hydrochloride:

TABLE 2

| Species of Animal | Dosage (mg/kg) | Administration | Effect |
|---|---|---|---|
| Horse | 0.03 | i.v. | light sedation, slight analgesia |
| | 0.03 | i.m. | light sedation, no analgesia |
| | 0.06 | i.v. | strong sedation, good analgesia |
| | 0.06 | i.m. | moderate sedation, rather weaker analgesia |
| | 0.07 | i.v. | strong sedation, good analgesia |
| | 0.08 | i.m. | strong sedation and good analgesia |
| Cattle (calf) | 0.006 | i.v. | low-level sedation, |
| | | i.m. | no analgesia |
| | 0.008 | i.m. | good sedation, deep |

TABLE 2-continued

| Species of Animal | Dosage (mg/kg) | Administration | Effect |
|---|---|---|---|
| | 0.009 | i.v. | sleep very good sedation, deep sleep, analgesia: not total |
| | 0.009 | i.m. | very good sedation, deep sleep, analgesia: as with i.v. |
| | 0.01 | i.v. | very good sedation, moderate analgesia |
| | 0.01 | i.m. | very good sedation, moderate analgesia |
| Calf | 0.01 | i.v. | as premedication for surgical interventions - hernia umbilicalis - 20 minutes after the injection the operation on the navel was carried out and the sedation and analgesia during and after the operation were judged to be good |
| | 0.04 | p.o. | very good depth of sedation, animal cannot be roused. |
| Pig | 0.01–0.03 | i.m. | weak sedation and analgesia |
| | 0.03–0.06 | i.m. | good sedation, rather weaker analgesia |
| | 0.06–0.1 | i.m. | very good sedation and good analgesia |
| | 0.01–1.0 | i.m. | strong sedation and very good analgesia |
| Poultry | 0.01–0.1 | i.m. | weak sedation |
| | 0.1–0.5 | i.m. | good sedation |
| | 0.5–1.0 | i.m. | very good sedation |
| | 0.5–1.0 | p.o. | good sedation |
| | 2.0 | i.m. | strong sedation |
| | 2.0 | p.o. | good sedation |

The following examples are intended to illustrate the invention and should not be construed as limiting it thereto.

EXAMPLES

EXAMPLE OF PREPARATION

EXAMPLE 1

2-[(2-Bromo-6-fluorophenyl)-imino]-imidazolidine hydrochloride (a) Starting product By reaction of 2-fluoroaniline with acetic anhydride, 2-fluoroacetanilide is obtained, m.p. 77°–78.5° C., which is converted by reaction with chlorosulfonic acid into 4-chlorosulfonyl-2-fluoroacetanilide, m.p. 110°–130° C. (crude product). Reaction with concentrated ammonia yields the corresponding sulfonamide, m.p. 162°–165° C., which is brominated and then desulfonylated with concentrated acid to yield the 2-bromo-6-fluoroaniline and at the same time saponified. The crude oily aniline is converted, without purification, with potassium thiocyanate/benzyl chloride and subsequent saponification with potassium hydroxide solution into N-(2-bromo-6-fluorophenyl)-thiourea, m.p. 145°–147° C., from which N-(2-bromo-6-fluorophenyl)-S-methyl-isothiuronium iodide is obtained by methylation with methyl iodide.

(b) End product

An amount of 6.7 gm (0.017 mol) N-(2-bromo-6-fluorophenyl)-S-methylisothiuromium iodide is refluxed with 1.7 ml (150%) of ethylenediamine in 20 ml of n-butanol for six hours with stirring. The mixture is then concentrated to dryness in vacuo, and the residue remaining is dissolved in dilute hydrochloric acid. It is extracted twice with ether (the ether extracts are discarded) and then fractionally extracted with ether at increasing pH values (alkalizing with dilute sodium hydroxide solution). The fractions which are pure according to thin layer chromatography are combined, dried over magnesium sulfate, and filtered over activated charcoal. By addition of ethereal hydrochloric acid until a congo acid reaction is obtained, the imidazolidine hydrochloride is precipitated. After suction filtration, washing with absolute ether, and drying, a yield of 2.7 gm of the title compound, m.p. 259°–262° C., is obtained, which corresponds to 53.6% of theory. The pKa value of the substance is 8.2

$C_9H_9BrFN_3 \times HCl$, molecular weight: 294.54.

FORMULATION EXAMPLES

EXAMPLE 2

Tablets

Each tablet has the following composition:

| Component | Amount (mg) |
|---|---|
| Active substance | 0.15 |
| Corn starch | 160.00 |
| Sec. calcium phosphate | 250.00 |
| Magnesium stearate | 9.85 |
| Total: | 420.00 |

Preparation

The individual ingredients are thoroughly mixed, and the mixture is granulated in conventional manner. The granules are compressed to form tablets weighing 420 mg, each containing 0.15 mg of active substance.

EXAMPLE 3

Gelatine capsules

The contents of each capsule has the following composition:

| Component | Amount (mg) |
|---|---|
| Active substance | 0.3 |
| Corn starch | 199.7 |
| Total: | 200.0 |

Preparation

The ingredients of the capsule contents are thoroughly mixed, and 200 mg batches of the mixture are packed into gelatine capsules of a suitable size. Each capsule contains 0.3 mg of the active substance.

EXAMPLE 4

Injection solution

The solution is prepared from the following:

| Component | Amount |
|---|---|
| Active substance | 1.5 parts |
| Sodium salt of ethylenediaminetetraacetic acid | 0.2 parts |
| Dist. water q.s. ad. | 100.0 parts |

Preparation

The active substance and sodium salt of ethylenediaminetetraacetic acid are dissolved in sufficient water and made up to the required volume with water. The solution is filtered to remove any suspended particles and then transferred into 2 ml ampules under aseptic conditions. Finally, the ampules are sterilized and sealed. Each ampule contains 30 mg of active substance.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A method of providing sedation with analgesic and bradycardiac effects to a warm-blooded animal in need of such sedation which comprises administering to said animal as active ingredient an effective amount of 2-((2-bromo-6-fluorophenyl)-imino)-imidazolidine or a pharmacologically acceptable acid addition salt thereof.

2. The method of claim 2 which comprises an effective amount of 2-((2-bromo-6-fluorophenyl)-imino)-imidazolidine hydrochloride.

3. The method of claim 1, wherein from about 0.002 to 5.0 mg/kg of active ingredient are administered.

4. The method of claim 3, wherein from about 0.006 to 0.8 mg/kg of active substance are administered.

5. The method of claim 1, wherein the active ingredient is administered to alleviate stress.

6. The method of claim 1, wherein the active ingredient is administered parenterally or orally or is added to fodder or drinking water.

* * * * *

UNITED STATES PATENT AND TRADEMARK OFFICE
CERTIFICATE OF CORRECTION

PATENT NO. : 4,624,960

DATED : November 25, 1986

INVENTOR(S) : OTTO KERN ET AL.

It is certified that error appears in the above-identified patent and that said Letters Patent is hereby corrected as shown below:

Column 6, line 3: "2" should read -- 1 --.

Signed and Sealed this

Twenty-fourth Day of February, 1987

*Attest:*

DONALD J. QUIGG

*Attesting Officer*   *Commissioner of Patents and Trademarks*